United States Patent
Murata et al.

(10) Patent No.: US 11,324,784 B2
(45) Date of Patent: May 10, 2022

(54) SLEEP-PROMOTING COMPOSITION, AND MEDICAL COMPOSITION AND FOOD BEVERAGE COMPOSITION USING SAID SLEEP-PROMOTING COMPOSITION

(71) Applicant: MORINAGA MILK INDUSTRY CO., LTD., Tokyo (JP)

(72) Inventors: Mai Murata, Kanagawa (JP); Junichi Minami, Kanagawa (JP); Akio Yamada, Kanagawa (JP); Tetsuya Kuhara, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 17/042,434

(22) PCT Filed: Mar. 22, 2019

(86) PCT No.: PCT/JP2019/012148
§ 371 (c)(1),
(2) Date: Sep. 28, 2020

(87) PCT Pub. No.: WO2019/188806
PCT Pub. Date: Oct. 3, 2019

(65) Prior Publication Data
US 2021/0077548 A1 Mar. 18, 2021

(30) Foreign Application Priority Data
Mar. 28, 2018 (JP) .............................. JP2018-062340

(51) Int. Cl.
*A61K 35/745* (2015.01)
*A23L 33/10* (2016.01)

(52) U.S. Cl.
CPC ............ *A61K 35/745* (2013.01); *A23L 33/10* (2016.08)

(58) Field of Classification Search
None
See application file for complete search history.

(56) References Cited

U.S. PATENT DOCUMENTS

| | | | |
|---|---|---|---|
| 2008/0044499 | A1 | 2/2008 | Ozeki et al. |
| 2014/0227318 | A1 | 8/2014 | Urade et al. |
| 2014/0248383 | A1 | 9/2014 | Urade et al. |
| 2019/0083549 | A1 | 3/2019 | Kobayashi et al. |
| 2021/0100853 | A1 | 4/2021 | Sakurai et al. |

FOREIGN PATENT DOCUMENTS

| | | | |
|---|---|---|---|
| CN | 106389960 | * | 2/2017 |
| JP | 2006-028051 | A | 2/2006 |
| JP | 2006-062998 | A | 3/2006 |
| JP | 2013-082641 | A | 5/2013 |
| WO | WO2005/097101 | A1 | 10/2005 |
| WO | WO2010/060722 | A1 | 6/2010 |
| WO | WO2013/051727 | A1 | 4/2013 |
| WO | WO2015/098441 | A1 | 7/2015 |
| WO | 2018/181069 | A1 | 10/2018 |

OTHER PUBLICATIONS

Wallis, A., et al., "Open-label pilot for treatment targeting gut dysbiosis in myalgic encephalomyelitis/chronic fatigue syndrome: neuropsychological symptoms and sex comparisons," J. Transl. Med. 2018;16:24:pp. 1-16.
Furihata, R., et al., "The association between sleep problems and perceived health status: A Japanese nationwide general population survey," Sleep Med. 2012;13:831-837.
Miyazaki, K., et al., "Dietary heat-killed Lactobacillus brevis SBC8803 promotes voluntary wheel-running and affects sleep rhythms in mice," Life Sci. 2014;111:47-52.
International Search Report for PCT Patent App. No. PCT/JP2019/012148 (dated May 28, 2019).
Evivie, S. E., et al., "Some current applications, limitations and future perspectives of lactic acid bacteria as probiotics," Food Nutr. Res. 2017;61(1):1318034, 17 pp.
Toda, K., et al., "Heat-Killed Bifidobacterium breve B-3 Enhances Muscle Functions: Possible Involvement of Increases in Muscle Mass and Mitochondrial Biogenesis," Nutrients 2020;12:219, 13 pp.
Riemann, D., et al., "European guideline for the diagnosis and treatment of insomnia," J. Sleep. Res. 2017;26:675-700.
Extended European Search Report for European Patent App. No. 19775012.8 (dated Nov. 9, 2021).

* cited by examiner

*Primary Examiner* — Vera Afremova
(74) *Attorney, Agent, or Firm* — Cermak Nakajima & McGowan LLP; Shelly Guest Cermak

(57) ABSTRACT

Provided is a novel sleep-promoting composition. Provided is a sleep-promoting composition comprising bacteria belonging to *Bifidobacterium breve* as an active ingredient. The sleep-promoting composition related to the present technology may prolong a sleep time by prolonging non-REM sleep and REM sleep, reducing a spontaneous behavior amount during sleep, or reducing an awakening time during sleep. The sleep-promoting composition related to the present technology may also reduce difficulty in daytime awakening. The sleep-promoting composition related to the present technology may be used for a medical composition or a food and beverage composition.

5 Claims, No Drawings

SLEEP-PROMOTING COMPOSITION, AND MEDICAL COMPOSITION AND FOOD BEVERAGE COMPOSITION USING SAID SLEEP-PROMOTING COMPOSITION

This application is a national phase entry under 35 U.S.C. § 371 of PCT Patent Application No. PCT/JP2019/012148, filed on Mar. 22, 2019, which claims priority under 35 U.S.C. § 119 to Japanese Patent Application No. 2018-062340, filed Mar. 28, 2018, both of which are incorporated by reference.

TECHNICAL FIELD

The present technology relates to a sleep-promoting composition, a medical composition, and a food and beverage composition using the sleep-promoting composition.

BACKGROUND ART

In modern society, due to mental stress in daily life or working, and a 24-hour-type lifestyle, people who suffer from insomnia are increasing. In a survey targeting Japanese people, the percentage of people suspected of having insomnia reached about 40%, and so is becoming a serious social problem (see Non-Patent Literature 1).

As dissatisfaction with quality of sleep, for example, trouble in falling asleep, having nightmares, feeling still sleepy when waking up, no feeling of deep sleep (feeling of sound sleep), remaining fatigued even after awakening, difficulty in staying awake during the daytime (feeling sleepy during the daytime), and the like are exemplified. Due to these sleep problems, work efficiency may be reduced, and there is also a risk of unexpected accidents. As the causes of these problems, not only a short sleep time, but also not having sleep of good quality may be mentioned. That is, this is because deep non-REM sleep cannot be obtained, that is, it takes a long time until the onset of non-REM sleep after going to bed (Sleep onset latency), non-REM sleep time is short, and an appropriate sleep pattern of REM sleep and non-REM sleep is disturbed. Therefore, it is considered that the demand for drugs for improving insomnia, for people who want comfortable and quality sleep, will further increase in the future.

For these, as means of improving sleep quality, the use of sleeping pills as medicines may be taken into consideration. However, in using sleeping pills, a doctor's diagnosis is required. In many cases, it is difficult to simply and safely use the sleeping pills because there are also side effects such as difficulty in waking up, defects of memory, and dependence. Also, among sleeping pills as medicines, there are also medicines that reduce non-REM sleep, such as sleeping pills mainly having benzodiazepines, barbituric acids, and hydrochloric acids. Thus, inversely, there are also things that reduce the quality of sleep if not correctly used. The use of other chemically synthesized drugs that alleviate mental stress, such as tranquilizers, antianxiety drugs, and sleeping pills can be a problem in that these are not suitable for daily or long-term use due to serious side effects or that they are habit-forming.

Also, as a method of coping with sleep improvement, coping methods such as improvement of lifestyle or mental training have also been tried, but their effectiveness is limited.

Besides medicines, research and development of sleep improvers from natural ingredients or foods/drinks have been actively conducted, and various things have been proposed. As active ingredients of such sleep improvers, for example, ingredients derived from plants of the genus *Withania* of the family Solanaceae (see Patent Literature 1), fermented processed products of daylilies (*Hemerocallis fulva*. var. *sempervirens*) (see Patent Literature 2), theanine derived from tea leaves (see Patent Literature 3), etc. may be mentioned. Also, S-adenoxyl methionine-containing yeast (see Patent Literature 4), an ash (*Fraxinus excelsior*) extract and an Siberian larch (*Larix sibirica*) extract (see Patent Literature 5), a composition containing α-lipoic acid and zinc (see Patent Literature 6), etc. have also been proposed.

In recent years, it has been reported that the intestinal environment is involved in signal transduction from the intestine to the brain, and the control of sleep, in which the intestine is a starting point.

For example, Patent Literature 7 discloses an effect of prolonging a non-REM sleep time and an effect of shortening a REM sleep time in a mouse to which *Bifidobacterium longum* ATCC BAA-999 is administered. Also, Non-Patent Literature 2 discloses that administration of lactic acid bacteria *Lactobacillus brevis* SBC8803 has an effect of regulating a circadian rhythm and promoting non-REM sleep.

CITATION LIST

Patent Literature

Patent Literature 1: JP-A-2006-028051
Patent Literature 2: JP-A-2006-062998
Patent Literature 3: WO2005/097101
Patent Literature 4: JP-A-2013-082641
Patent Literature 5: WO2013/051727
Patent Literature 6: WO2015/098441
Patent Literature 7: WO2010/060722

Non-Patent Literature

Non-Patent Literature 1: Sleep Med 2012; 13 (7):831-837
Non-Patent Literature 2: Life Science 2014; 111 (102):47-52

SUMMARY OF INVENTION

Technical Problem

As described above, to date, improving non-REM sleep by ingesting probiotics, microbial cells, or fermented products have been reported, but it is known that probiotics exhibit different physiological actions depending on the strain. Thus, no consistent results have been obtained. No component that reduces awakening midway during sleep and promotes both non-REM sleep and REM sleep has been reported.

Therefore, a main object of the present technology is to provide a novel sleep-promoting composition.

Means to Solve the Problem

That is, first, the present technology provides a sleep-promoting composition including bacteria belonging to *Bifidobacterium breve* as an active ingredient.

In the sleep-promoting composition related to the present technology, as for the above bacteria belonging to *Bifidobacterium breve*, *Bifidobacterium breve* MCC1274 (FERM BP-11175) may be used.

The sleep-promoting composition related to the present technology may prolong sleep time by promoting sleep.

More specifically, the sleep-promoting composition related to the present technology may prolong sleep time by prolonging both non-REM sleep and REM sleep, reducing the amount of spontaneous or involuntary behavior or movement during sleep, or reducing time spent awake during the time when sleep is desired.

The sleep-promoting composition related to the present technology may reduce difficulty in staying awake during the daytime.

The sleep-promoting composition related to the present technology may be used in a medical composition or a food and beverage composition.

Advantageous Effects of Invention

According to the present technology, a novel sleep-promoting composition may be provided.

The effects described herein are not necessarily limited and may be any of the effects described in this specification.

DESCRIPTION OF EMBODIMENTS

Hereinafter, a preferred embodiment for carrying out the present technology will be described. The embodiment described below is an example of a representative embodiment of the present technology, by which the scope of the present technology is not narrowly construed.

1. Sleep-Promoting Composition

The sleep-promoting composition of the present technology contains bacteria belonging to *Bifidobacterium breve*, as an active ingredient.

*Bifidobacterium breve* is a bacterial species belonging to the genus *Bifidobacterium*. *Bifidobacterium breve* is mainly found in a large amount within the large intestine of an infant, and is known as an infant-type bacterium of the genus *Bifidobacterium* together with *Bifidobacterium longum* subsp. *infantis* and the like among bacterial species belonging to the genus *Bifidobacterium*.

The sleep-promoting composition of the present technology is excellent in regards to safety because the active ingredient *Bifidobacterium breve* is mainly found in a large amount within the large intestine of an infant, and is very useful because there is little need to worry about side effects even when continuously administered for a long period of time. Further, the safety is high even when used in combination with other drugs.

As for bacteria belonging to *Bifidobacterium breve*, for example, *Bifidobacterium breve* MCC1274 (FERN BP-11175), M-16V (NITE BP-02622), UCC2003, YIT4010, YIT4064, BBG-001, BR-03, B632 (DSMZ 24706), C50, Bb99 (DSM 13692), R0070, ATCC15700, ATCC15698, DSM 24732, etc. may be mentioned, but among them, it is desirable to use MCC1274 (FERN BP-11175), and M-16V (NITE BP-02622).

MCC1274 was deposited with a deposit number of IPOD FERN BP-11175 at Patent Organism Depository Center, National Institute of Advanced Industrial Science and Technology (Central 6, 1-1-1 Higashi, Tsukuba, Ibaraki, 305-8566, Japan (at present, IPOD Patent Organism Depository Center, National Institute of Technology and Evaluation (NITE-IPOD): Room No. 120, 2-5-8 Kazusakamatari Kisarazu Chiba 292-0818, Japan)) on Aug. 25, 2009.

M-16V was internationally deposited under the Budapest Treaty with a deposit number of NITE BP-02622 at Patent Microorganism Depository Center, National Institute of Technology and Evaluation (Room No. 122, 2-5-8 Kazusakamatari Kisarazu Chiba 292-0818) on Jan. 26, 2018.

In the present technology, it is desirable to use *Bifidobacterium breve* MCC1274 (FERN BP-11175) as the above bacteria belonging to *Bifidobacterium breve*.

The strain specified by the above-exemplified strain name is not limited to a strain itself that has been deposited or registered in a predetermined institution with the corresponding strain name (hereinafter, for convenience of explanation, also referred to as a "deposited strain"), but also includes a strain substantially equivalent thereto (also referred to as a "derivative strain" or an "induced strain"). That is, for example, "*Bifidobacterium breve* MCC1274 (FERM BP-11175)" is not limited to a strain itself that has been deposited in the above depository with a deposit number of MCC1274 (FERM BP-11175), but also includes a strain substantially equivalent thereto.

For a strain, "the strain substantially equivalent to the above deposited strain" refers to a strain belonging to the same species as the above deposited strain, in which the effect of the present invention, that is, a sleep promoting effect may be obtained. The strain substantially equivalent to the above deposited strain may be, for example, a derivative strain whose parent strain is the corresponding deposited strain. The derivative strain may include a strain bred from the deposited strain or a strain naturally occurring from the deposited strain.

As for the substantially identical strains and derivative strains, the following strains may be mentioned:

(1) a strain determined as an identical strain by an RAPD method (Randomly Amplified Polymorphic DNA) or a PFGE method (pulsed-field gel electrophoresis) (described in Probiotics in food/Health and nutritional properties and guidelines for evaluation 85, Page 43);

(2) a strain that has only the genes derived from the corresponding deposited strain, has no foreign-derived genes, and has a DNA identity of 95% or more;

(3) a strain bred from the corresponding strain (including genetic engineering alterations, mutations, and natural mutations), and a strain having the same trait.

The sleep-promoting composition of the present technology may promote sleep, and prolong sleep time. More specifically, the sleep-promoting composition related to the present technology may prolong sleep time by prolonging non-REM sleep and REM sleep, reducing spontaneous or involuntary behavior or movement during sleep, or reducing time spent awake during the night when it is desired to be asleep. For example, when the sleep-promoting composition of the present technology is ingested, it is possible to continuously sleep for a long time, i.e. stay asleep, which reduces awakening midway during the night when sleeping. Thus, the quality of sleep is improved, and deep sleep may be achieved.

Also, the sleep-promoting composition related to the present technology may also reduce the difficulty of awakening in the morning or staying awake during the day.

Also, the sleep-promoting composition related to the present technology also has a sedative effect.

The sleep-promoting composition related to the present technology promotes sleep, and thus may be used for preventing and/or treating symptoms or diseases that occur as a result of poor sleep. As for the symptoms or the diseases that occur as a result of poor sleep, for example, insomnia (trouble in falling asleep, inability to get back to sleep after awakening midway, early morning awakening, inability to sleep deeply), hypersomnia (being sleepy and therefore embarrassed during the daytime, being cautioned for dozing off), a circadian rhythm sleep disorder, a restless legs syndrome (*anxietas tibiarum*), snoring, a sleep apnea syndrome, parasomnia, narcolepsy, sleepwalking (somnambulism), confusion arousal, a sleep terror disorder (night terror), a rhythmic movement disorder, cramps during sleep, sleep talking, night crying, infant colic (colic), nocturnal leg cramps, nightmare, sleep paralysis, sleep-related penile erectile dysfunction, an REM sleep behavior disorder, bruxism, nocturnal enuresis, paroxysmal dystonia, periodic limb movement disorder, sudden infant death syndrome (SIDS), etc. may be mentioned.

Also, the sleep-promoting composition related to the present technology may also promote sleep under a specific situation. Specifically, for example, this is effective when it is not possible to sleep soundly for a long time due to menopause, being elderly, lactation, shift workers, jet lag caused by overseas travel, social jet lag after a holiday, awakening caused by an optical stimulation by smart phones or PCs (technostress insomnia), or the like.

The target of the sleep-promoting composition related to the present technology is not particularly limited, and application to animals including humans is possible. For example, the use is possible for trouble in falling asleep (a hypnagogic disorder), waking up during night after falling asleep once (awakening midway), waking up earlier than desired (early morning awakening), and not having feeling of satisfaction such as 'got enough sleep' (a deep sleep disorder). Also, the target sex, the target age, etc. are not particularly limited, but, for humans, the use is possible for infants who have trouble in falling asleep, and middle and elderly people who are prone to sleep disorders.

Also, in particular, a particularly effective use is possible for ages over 35, preferably ages over 40, more preferably middle and older ages over 45.

The sleep-promoting composition related to the present technology may contain a culture including bacteria belonging to *Bifidobacterium breve*, as bacteria belonging to *Bifidobacterium breve*, which is an active ingredient thereof.

A medium for culturing *Bifidobacterium breve* to be used in the present technology is not particularly limited, and a medium generally used for culturing bacteria belonging to the genus *Bifidobacterium* may be used.

That is, as for carbon sources, for example, saccharides such as glucose, galactose, lactose, arabinose, mannose, sucrose, starch, starch hydrolysate, and blackstrap molasses may be used depending on the assimilability. As for nitrogen sources, for example, ammonia, ammonium salts such as ammonium sulfate, ammonium chloride, and ammonium nitride, or nitrates may be used. Also, as for inorganic salts, for example, sodium chloride, potassium chloride, potassium phosphate, magnesium sulfate, calcium chloride, calcium nitride, manganese chloride, ferrous sulfate, and the like may be used. Also, organic components such as peptone, soybean powder, defatted soybean meal, meat extract, and yeast extract may be used.

The culturing condition is not particularly limited as long as the effect of the present technology is not impaired, but, for example, the culturing temperature is generally 25 to 50° C., preferably 35 to 42° C. Also, it is desirable to carry out the culturing under anaerobic conditions, and the culturing may be carried out while, for example, an anaerobic gas such as a carbon dioxide gas is aerated. Also, the culturing may be carried out under slightly aerobic conditions in liquid static culture.

As for the present microbial cells, the culture obtained by culturing may be used as it is, or may be used through dilution or concentration, or microbial cells collected from the culture may be used. Also, various additional operations such as heating and freeze-drying may be carried out after culturing as long as the effect of the present invention is not impaired. Also, the present microbial cells may be live bacteria or dead bacteria. In the case of live bacteria, it is desirable to perform treatment by a bacterial fluid freezing method, a spray drying method, a freeze-drying method, or an oil drop method. The dead bacteria may include dead bacteria sterilized by heating, freeze-drying, or the like. Other methods for preparing dead microbial cells may include a spray drying method, a retort sterilization method, a freeze drying method, a UHT sterilization method, a pressure sterilization method, a high pressure steam sterilization method, a dry heat sterilization method, a circulating steam sterilization method, an electromagnetic wave sterilization method, an electron beam sterilization method, a high frequency sterilization method, a radiation sterilization method, an ultraviolet sterilization method, an ethylene oxide gas sterilization method, a hydrogen peroxide gas plasma sterilization method, a chemical sterilization method (an alcohol sterilization method, a formalin fixation method, an electrolyzed water treatment method), and the like. Also, the present microbial cells may be a crushed product. The crushed product may be one obtained by crushing live bacteria, may be one obtained by crushing dead bacteria, and may be one obtained by performing heating, freeze-drying, or the like after crushing.

Also, for the crushing, crushing through, for example, physical crushing, enzyme lysis treatment, chemical treatment, self-dissolution treatment, or the like, which uses methods and devices conventionally known in the present technical field, may be selected.

Physical crushing may be accomplished by either treating the microbial cell suspension treating the microbial cell powder. As an example of physical crushing, crushing by stirring using an ultrasonic homogenizer, a homogenizer, a ball mill, a beads mill, a dyno mill, a planetary mill, etc., crushing by pressurization using a jet mill, a French press, a cell crusher, etc. or crushing by damaging microbial cells through filter filtration may be selected.

In the enzyme lysis treatment, for example, an enzyme such as lysozyme may be used to destroy the cell structure of *lactobacilli* microbial cells.

In the chemical treatment, a surfactant such as soybean phospholipid or glycerin fatty acid ester may be used to destroy the cell structure of *lactobacilli* microbial cells.

In the self-dissolution treatment, *lactobacilli* microbial cells may be dissolved by enzymes of some *lactobacilli* themselves.

In the present invention, physical crushing is preferred because there is no need to add other chemicals or compounds.

In this specification, "culture" includes a culture supernatant.

The sleep-promoting composition related to the present technology may include only the above active ingredient, or may be a composition in which the above active ingredient is blended with optional ingredients other than the active ingredient.

The above optional ingredients are not particularly limited, and additives that have conventionally been blended with medicines (for example, a formulation carrier to be described below, etc.) may be blended.

2. Specific Form of Sleep-Promoting Composition Related to the Present Technology The sleep-promoting composition related to the present technology may be used in the form of foods/drinks, medicines, quasi-drugs, feeds, and the like.

The application of this embodiment may be for a therapeutic purpose use, or a non-therapeutic purpose use.

The "non-therapeutic purpose" does not include a medical act, that is, an act of treating a human body by treatment. For example, health promotion, aesthetic treatment, and the like may be mentioned.

"Improvement" refers to improvement of a disease, a symptom or a condition; prevention or delay of deterioration of a disease, a symptom or a condition; or reversal, prevention or delay of progression of a disease or a symptom.

"Prevention" refers to prevention or delay of the onset of a disease or a symptom in the application target, or risk reduction of a disease or a symptom of the application target.

<Food/Drink>

The sleep-promoting composition related to the present technology may be added to a conventionally known food/drink in preparation, or may be mixed with food/drink raw materials so as to produce a new food/drink.

The food/drink using the sleep-promoting composition related to the present technology may have any form such as liquids, pastes, solids, or powder, and not only tablet confectioneries, liquid foods, etc., but also, for example, flour products, instant foods, processed agricultural products, processed seafood products, processed livestock products, milk/dairy products, oils and fats, basic seasonings, complex seasonings/foods, frozen foods, confectioneries, drinks, commercially available products other than these, etc. may be mentioned.

Examples of the flour product may include bread, macaroni, spaghetti, noodles, cake mix, frying powder, breadcrumbs, etc.

Examples of the instant food may include instant noodles, cup noodles, retort/cooked foods, cooked cans, microwave foods, instant soup/stew, instant miso soup/clear soup, canned soup, freeze-dried foods, other instant foods, etc.

Examples of the processed agricultural product may include canned agricultural products, canned fruits, jams/marmalades, pickles, cooked beans, dried agricultural products, cereals (processed grain products), etc.

Examples of the processed seafood product may include canned seafoods, fish-flesh hams/sausages, seafood paste products, seafood delicacies, tsukudani, etc.

Examples of the processed livestock product may include canned livestock/pastes, meat hams/sausages, etc.

Examples of the milk/dairy product may include fermented milk, processed milk, milk drinks, yogurts, lactic beverages, cheese, ice creams, modified milk powder, cream, modified milk powder for nursery, dietary supplements for infants, other dairy products, etc.

Examples of the oil and fat may include butter, margarines, vegetable oils, etc.

As the basic seasoning, for example, soy sauces, miso, sauces, processed tomato seasonings, mirins, vinegars, etc. may be mentioned, and as the complex seasoning/food, cooking mix, curry sauces, seasoned soups, dressings, liquid condiments, spices, other complex seasonings, etc. may be mentioned.

Examples of the frozen food may include frozen food ingredients, semi-cooked frozen foods, cooked frozen foods, etc.

Examples of the confectionery may include caramels, candies, chewing gums, chocolates, cookies, biscuits, cakes, pies, snacks, crackers, Japanese sweets, rice confectioneries, bean confectioneries, dessert confectioneries, other confectioneries, etc.

Examples of the drink may include carbonated drinks, natural fruit juices, fruit juice drinks, fruit juice-containing soft drinks, pulp drinks, granule-containing fruit drinks, vegetable-based drinks, soymilk, soymilk drinks, coffee drinks, tea drinks, powdered drinks, concentrated drinks, sports drinks, nutritional drinks, alcohol drinks, other favorite drinks, etc.

Examples of the other commercially available foods may include baby foods, furikake, ochazuke seaweed, etc.

The food and beverage composition of the present invention may be produced by adding the present microbial cells to raw materials of a normal food/drink, and may be produced in the same manner as the normal food/drink except that the present microbial cells are added. The addition of the present microbial cells may be carried out at any stage in the production process of the food and beverage composition. Also, the food and beverage composition may be produced through a fermentation process with these added microbial cells. As for such a food and beverage composition, lactic beverage, fermented milk, and the like may be mentioned.

As for the raw materials of the food and beverage composition, raw materials used for a normal food/drink may be used. The produced food and beverage composition may be orally ingested.

Also, in the food and beverage composition of the present invention, it is possible to use ingredients having probiotic effects, which are conventionally known or are to be found in the future, or ingredients that assist the probiotic effects as long as the effect of the present invention is not impaired. For example, the food and beverage composition of the present invention may be produced by blending the present microbial cells with components such as: various proteins such as whey protein, casein protein, soybean protein, or pea protein, or mixtures or decomposed products thereof; amino acids such as leucine, valine, isoleucine or glutamine; vitamins such as vitamin B6 or vitamin C; creatine; citric acid; fish oils; or oligosaccharides such as isomalto oligosaccharide, galacto oligosaccharide, xylo oligosaccharide, soybean oligosaccharide, fructo oligosaccharide, or lactulose.

The content of bacteria belonging to *Bifidobacterium breve* in the food/drink related to the present technology may be freely set as long as the effect of the present technology is not impaired. In the present technology, in particular, in the food/drink including bacteria belonging to *Bifidobacterium breve*, it is more preferable that the content is $1 \times 10^3$ to $1 \times 10^{12}$ CFU/g with respect to a final composition of the food/drink. Also, it is desirable that the daily dose to be added is at least $1 \times 10^3$ CFU/day or more, more preferably $1 \times 10^6$ CFU/day or more, more preferably $1 \times 10^8$ CFU/day or more, more preferably $2 \times 10^{10}$ CFU/day or more, or more. "cfu" indicates a colony forming unit. When the present microbial cells are dead bacteria, cfu/g or cfu/ml may be replaced with individual cells/g or individual cells/ml. When the present microbial cells are a crushed product, it is possible to express the number of bacteria (individual cells/g) before crushing, in terms of weight.

Functionality Labeled Food/Drink

Also, the foods/drinks and the like defined in the present technology may also be provided or sold as foods/drinks labeled with a specific application (particularly, a health application) or a function.

The action of "labeling" includes all actions of informing consumers of the above application, and all expressions correspond to the action of "labeling" of the present technology regardless of the purpose of a label, the contents of a label, and a target object and a medium of labeling, as long as the above application may be recalled or analogized.

Also, it is desirable that the "labeling" allows the consumers to directly recognize the above application. Specifically, assignment and delivery of a product or a product package related to a food or a drink (on which the above application is described), and display and import of the assignment or delivery; and displaying or distributing advertisements, a price list, or a transaction document related to the product, on which the above application is described, or providing information having these as contents, on which the above application is described, by an electromagnetic (the Internet, etc.) method may be mentioned.

Meanwhile, as for the label contents, a label permitted by the government or the like (for example, a label or the like that is approved in accordance with various systems specified by the government, and is applied in the form based on such approval) is preferred. Also, it is desirable that such label contents are attached to packaging, containers, catalogs, pamphlets, advertising materials at a sales site such as a POP, other documents and the like.

Also, as for the "label," labels for health foods, functional foods, foods for patients, enteral nutritional foods, special purpose foods, health functional foods, foods for specified health uses, functionality labeled foods, nutritionally functional foods, quasi-drugs, etc. may also be mentioned. Among these, particularly, labels approved by the Consumer Affairs Agency, for example, labels or the like approved by systems for foods for specified health uses, systems for functionality labeled foods, and systems similar to these, may be mentioned. More specifically, labels for foods for specified health uses, labels for foods for conditional specified health uses, labels for functionality labeled foods, labels to the effect that the structure or function of a body is affected, labels on disease risk reduction, and the like may be mentioned. Among these, typical examples include labels for foods for specified health uses, which are stipulated in the Enforcement Regulations of Health Promotion Law (Apr. 30, 2003, Japanese Ministry of Health, Labor, and Welfare Ordinance No. 86) (particularly, labels for health applications), labels for functionality labeled foods, which are stipulated in Food Labeling Act (2013, Law No. 70), and labels similar thereto.

Words used for carrying out the above described labeling are not limited to only words for sleep promotion or the like. It is needless to say that even other words are included in the scope of the present technology as long as they are words indicating the effect of prevention, treatment and/or improvement of various diseases or symptoms related to sleep promotion. Examples of these words may include "for those who cannot sleep," "for those who want to improve quality of sleep," "for those who worry about falling asleep," "for those feel fatigue when waking up," and the like, and it is also possible to perform labeling based on various applications, which may allow consumers to recognize the effect of sleep promotion.

Also, for example, it is possible to employ a method in which extracted breast milk, to which the present microbial cells are added, is orally ingested or ingested through a nasogastric feeding tube, etc. by newborn babies or infants.

Also, in the food and beverage composition of the present invention, it is possible to use ingredients having prebiotic effects, which are conventionally known or are to be found in the future, or ingredients that assist the prebiotic effects as long as the effect of the present invention is not impaired. For example, the food and beverage composition of the present invention may be produced by blending the present microbial cells with components such as: various proteins such as whey protein, casein protein, soybean protein, or pea protein, or mixtures or decomposed products thereof; amino acids such as leucine, valine, isoleucine or glutamine; vitamins such as vitamin B6 or vitamin C; creatine; citric acid; fish oils; or oligosaccharides such as isomalto oligosaccharide, galacto oligosaccharide, xylo oligosaccharide, soybean oligosaccharide, fructo oligosaccharide, lactulose, or human milk oligosaccharide (HMO). As for the human milk oligosaccharide that may be used in the present invention, neutral human milk oligosaccharides such as 2'-fucosyllactose, 3-fucosyllactose, 2',3-difucosyllactose, lacto-N-triose II, lacto-N-tetraose, lacto-N-neotetraose, lacto-N-fucopentaose lacto-N-neofucopentaose, lacto-N-fucopentaose lacto-N-fucopentaose III, lacto-N-fucopentaose V, lacto-N-neofucopentaose V, lacto-N-difucohexaose lacto-N-difucohexaose II, 6'-galactosyl lactose, 3'-galactosyl lactose, lacto-N-hexaose, and lacto-N-neohexaose; and acidic human milk oligosaccharides such as 3'-sialyllactose, 6'-sialyllactose, 3-fucosyl-3'-sialyllactose, and disialyllacto-N-tetraose may be used.

As for the foods/drinks related to the present technology, modified milk powder for babies may be exemplified. The modified milk powder for babies refers to modified milk powder for babies, which targets 0 to 12-month-old babies, follow up milk which targets babies after 6 to 9 months and young infants (up to 3 years), modified milk powder for low birth weight infants, which targets newborn babies (low birth weight infants) weighing less than 2500 g at birth, various therapeutic milks used for treatment of children having pathological conditions such as milk allergy or lactose intolerance, or the like. Also, this composition may be applied to health functional foods or foods for patients. A health functional food system is provided for not only general foods but also foods in the form of tablets, capsules, etc., as targets, on the basis of domestic and foreign trends, and consistency with a traditional system for foods for specified health uses, and is composed of two types such as types of foods for specified health uses (individual permission type) and nutritionally functional foods (standard reference type).

As for the foods/drinks related to the present technology, mother's milk (modified milk powder) or dietary supplements exclusively for mothers in pregnancy and lactation may be mentioned. Mother's milk refers to milk or the like which is blended with nutrition required for pregnancy and lactation in a balanced way.

Specifically, the modified milk powder of the present technology may be produced by, for example, the following method.

That is, the present technology provides a method of producing sleep promoting milk powder, in which microbial cell powder including bacteria belonging to *Bifidobacterium breve* is mixed with prebiotics and/or milk powder to obtain the sleep promoting milk powder.

Specifically, for example, there is provided a method of producing sleep promoting milk powder, which includes the following steps (A) to (C):

(A) a step of culturing bacteria belonging to *Bifidobacterium breve* in a medium including a milk component to obtain a culture;

(B) a step of subjecting the above culture to spray-drying and/or freeze-drying to obtain microbial cell powder; and (C) a step of mixing the above microbial cell powder with prebiotics to obtain sleep promoting milk powder.

Also, the present technology provides a method of producing sleep promoting milk powder, which includes the following step (A):

(A) a step of mixing prebiotics, bacteria belonging to *Bifidobacterium breve*, and a milk component to obtain milk powder.

Also, specifically, the food composition of the present technology may be, for example, a sleep promoting supplement. The sleep promoting supplement may be produced by, for example, the following method.

That is, the present technology provides a method of producing a sleep promoting supplement, which includes the following steps (A) and (B):

(A) a step of mixing bacteria belonging to *Bifidobacterium breve*, and an excipient to obtain a mixture; and (B) a step of tableting the above mixture.

In any of the above production methods, ingredients other than the ingredients mentioned in the above steps may be properly used in combination.

<Medicine, Quasi-Drug>

The sleep-promoting composition related to the present technology may be added to a conventionally known medicine or quasi-drug (hereinafter, also referred to as a "medicine, etc.") in preparation, or may be mixed with raw materials of the medicine, etc. so as to produce a new medicine, etc.

When the sleep-promoting composition related to the present technology is blended with the medicine, etc., this medicine, etc. may be properly formulated into a desired dosage form according to an administration method such as oral administration or parenteral administration. The dosage form is not particularly limited, but in the case of oral administration, it is possible to formulate, for example, solid preparations such as powder, granules, tablets, troches, and capsules; and liquid preparations such as solutions, syrups, suspensions, and emulsions. In the case of parenteral administration, it is possible to formulate, for example, suppositories, spray, inhalants, ointment, patches, injections, and the like. In the present technology, formulation of a dosage form for oral administration is preferred.

The formulation may be properly carried out according to the dosage form by a conventionally known method.

In the formulation, the formulation may be performed by properly blending with a formulation carrier. Also, in addition to the sleep-promoting composition of the present technology, components generally used for formulation, such as an excipient, a pH adjuster, a colorant, and a corrigent, may be used. Also, components having an effect of preventing, improving and/or treating diseases or symptoms, which are conventionally known or to be found in the future, may be properly used in combination depending on their purpose.

As for the formulation carrier, various organic or inorganic carriers may be used depending on the dosage forms. In the case of solid preparations, examples of the carrier may include excipients, binders, disintegrants, lubricants, stabilizers, corrigents/flavoring agents, etc.

Examples of the excipient may include sugar derivatives such as lactose, white sugar, glucose, mannitol, and sorbitol; starch derivatives such as corn starch, potato starch, α-starch, dextrin, and carboxymethyl starch; cellulose derivatives such as crystalline cellulose, hydroxypropyl cellulose, hydroxypropyl methyl cellulose, carboxymethyl cellulose, and carboxymethyl cellulose calcium; gum arabic; dextran; pullulan; silicate derivatives such as light anhydrous silicic acid, synthetic aluminum silicate, and magnesium aluminometasilicate; phosphate derivatives such as calcium phosphate; carbonate derivatives such as calcium carbonate; and sulfate derivatives such as calcium sulfate.

Examples of the binder may include gelatin; polyvinylpyrrolidone; macrogol and the like, in addition to the above excipients.

Examples of the disintegrant may include cellulose derivatives or chemically modified starch such as sodium croscarmellose, sodium carboxymethyl starch, and cross-linked polyvinylpyrrolidone, in addition to the above excipients.

Examples of the lubricant may include talc; stearic acid; metallic stearates such as calcium stearate, and magnesium stearate; colloidal silica; waxes such as bee gum, and spermaceti; boric acid; glycol; carboxylic acids such as fumaric acid and adipic acid; carboxylic acid sodium salts such as sodium benzoate; sulfates such as sodium sulfate; leucine; lauryl sulfates such as sodium lauryl sulfate, and magnesium lauryl sulfate; silicic acids such as silicic acid anhydride, and silicic acid hydrate; and starch derivatives.

Examples of the stabilizer may include paraoxybenzoic acid esters such as methylparaben and propylparaben; alcohols such as chlorobutanol, benzyl alcohol, and phenylethyl alcohol; benzalkonium chloride; acetic anhydride; and sorbic acid.

Examples of the corrigent/flavoring agent may include sweeteners, acidulants, flavors, etc.

As for the carrier to be used in the case of liquid preparations for oral administration, a solvent such as water, a corrigent/flavoring agent, etc. may be mentioned.

The content of bacteria belonging to *Bifidobacterium breve* in the medicine, etc. related to the present technology may be freely set as long as the effect of the present technology is not impaired.

The amount of the present microbial cells in a medical composition is properly set according to dosage forms, usage, target age, sex, diseases or syndromes, types of symptoms or disorders, degrees thereof, other conditions, and the like, but in general, it is more desirable to contain $1\times10^3$ to $1\times10^{12}$ CFU/g. Also, it is desirable that the daily dose is at least $1\times10^3$ CFU/day or more, more preferably $1\times10^6$ CFU/day or more, more preferably $1\times10^8$ CFU/day or more, more preferably $2\times10^{10}$ CFU/day or more, or more. When the present microbial cells are dead bacteria, cfu/g or cfu/ml may be replaced with individual cells/g or individual cells/ml. When the present microbial cells are a crushed product, cfu/g or cfu/ml, or individual cells/g or individual cells/ml may be replaced with a crushed product of live bacteria or dead bacteria of cfu/g or cfu/ml, or individual cells/g or individual cells/ml as above.

<Feed>

The sleep-promoting composition related to the present technology may be added to a conventionally known feed in preparation, or may be mixed with raw materials of the feed so as to produce a new feed.

When the sleep-promoting composition related to the present technology is blended with the feed, examples of raw materials of the feed may include cereals such as corn, wheat, barley, and rye; brans such as wheat bran, barley bran, rice bran, and defatted rice bran; by-product feeds such as corn gluten meal and corn germ meal; animal feeds such as skim milk powder, whey, fish meal, and bone meal; yeasts such as beer yeast; mineral feeds such as calcium phosphate, and calcium carbonate; oils and fats; amino acids; and sugars. Also, examples of the form of the above feed may include pet feeds (pet foods and the like), livestock feeds, fish feeds, and the like.

The amount of bacteria belonging to *Bifidobacterium breve* in the feed related to the present technology may be freely set according to a body weight, etc. as long as the effect of the present technology is not impaired.

The amount of the present microbial cells in a feed composition is properly set according to dosage forms, usage, target age, sex, diseases or syndromes, types of symptoms or disorders, degrees thereof, other conditions, and the like, but in general, it is more desirable to contain $1\times10^3$ to $1\times10^{12}$ CFU/g. Also, it is desirable that the daily dose is at least $1\times10^3$ CFU/day or more, more preferably $1\times10^6$ CFU/day or more, more preferably $1\times10^8$ CFU/day or more, more preferably $2\times10^{10}$ CFU/day or more, or more. When the present microbial cells are dead bacteria, cfu/g or cfu/ml may be replaced with individual cells/g or individual cells/ml. When the present microbial cells are a crushed product, cfu/g or cfu/ml, or individual cells/g or individual cells/ml may be replaced with a crushed product of live bacteria or dead bacteria of cfu/g or cfu/ml, or individual cells/g or individual cells/ml as above.

The present technology may also employ the following configurations.

[1] A sleep-promoting composition comprising bacteria belonging to *Bifidobacterium breve* as an active ingredient.

[2] In the sleep-promoting composition of [1], the above bacteria are *Bifidobacterium breve* MCC1274 (FERM BP-11175).

[3] The sleep-promoting composition of [1] or [2] prolongs sleep time.

[4] The sleep-promoting composition of [3] prolongs both non-REM sleep and REM sleep.

[5] The sleep-promoting composition of [3] or [4] reduces the amount of spontaneous or involuntary behavior or movement during sleep.

[6] The sleep-promoting composition of any one of [1] to [5] reduces time spent awake during the time when it is desired to sleep.

[7] The sleep-promoting composition of any one of [1] to [6] reduces difficulty in staying awake during the daytime.

[8] The sleep-promoting composition of any one of [1] to [7] is a medical composition.

[9] The sleep-promoting composition of any one of [1] to [7] is a food composition.

[10] Use of bacteria belonging to *Bifidobacterium breve* in a sleep promoting agent, a sleep promoting medicine, or a sleep promoting food/drink.

[11] A sleep promoting method including administering bacteria belonging to *Bifidobacterium breve* to a subject.

[12] A sleep promoting method including administering bacteria belonging to *Bifidobacterium breve* to a person over 35 years old.

[13] Use of bacteria belonging to *Bifidobacterium breve* in preventing, treating and/or improving insomnia (trouble in falling asleep, inability to get back to sleep after awakening midway, early morning awakening, inability to sleep deeply), hypersomnia (being sleepy and embarrassed during daytime, being cautioned for dozing off), a circadian rhythm sleep disorder, a restless legs syndrome (*anxietas tibiarum*), snoring, a sleep apnea syndrome, parasomnia, narcolepsy, sleepwalking (somnambulism), confusion arousal, a sleep terror disorder (night terror), a rhythmic movement disorder, cramps during sleep, sleep talking, night crying, infant colic (colic), nocturnal leg cramps, nightmare, sleep paralysis, sleep-related penile erectile dysfunction, an REM sleep behavior disorder, bruxism, nocturnal enuresis, paroxysmal dystonia, a periodic limb movement disorder, a sudden infant death syndrome (SIDS), etc., which occur under poor sleep.

[14] A method of producing sleep promoting milk powder, which includes the following steps (A) to (C):

(A) a step of culturing *Bifidobacterium breve* in a medium comprising a milk component to obtain a culture;

(B) a step of subjecting the above culture to spray-drying and/or freeze-drying to obtain microbial cell powder; and (C) a step of mixing the above microbial cell powder with prebiotics to obtain sleep promoting milk powder.

[15] A method of producing sleep promoting milk powder, which includes the following step (A):

(A) a step of mixing prebiotics, *Bifidobacterium breve*, and a milk component to obtain milk powder.

[16] The method described in [14] or [15], the above milk component is a milk protein.

[17] The method described in any one of [14] to [16], the above milk protein is at least one component selected from the group including whey, whey hydrolysate, and casein.

[18] A method of producing a sleep promoting supplement, which includes the following steps (A) and (B):

(A) a step of mixing *Bifidobacterium breve*, and an excipient to obtain a mixture; and (B) a step of tableting the above mixture.

EXAMPLES

Hereinafter, the present technology will be described in more detail on the basis of the following Examples. Examples described below are a representative Examples of the present technology, by which the scope of the present technology should not be narrowly construed.

Experimental Example 1

In Experimental Example 1, a sleeping animal model was used to verify the sleep promoting effect of bacteria belonging to *Bifidobacterium breve*.

<Production of Test Sample>

A culture solution of *Bifidobacterium breve* MCC1274 (FERN BP-11175) as an example of bacteria belonging to *Bifidobacterium breve* was concentrated and dried to obtain a dried product of live bacteria.

<Sleeping Animal Model>

By using Slc: Wistar rats (male, 10 weeks old), the effect of administration of a test sample on sleep of animals was examined. Rats were purchased from Japan SLC Inc. The rats were bred under a light-dark cycle with an interval of 12 hours (5:00 am; start time of light period), under an environment of room temperature 23±3° C., and humidity 55±15%. As for a feed, unsterilized MF solid feed of ORIENTAL YEAST Co., Ltd. was used, and free feeding and free drinking were permitted. Under somnopentyl anesthesia, the hair of the rat was shaved from the neck to the back by a hair trimmer. After sterilization and incision, a triaxial acceleration sensor for movement amount measurement and an electrode for wireless measurement were embedded and retained. The incision part was disinfected and then sutured with a suture, and the incision part and the suture part were subjected to analgesic treatment by application of post-operative Marcain® injection 0.25%. After the operation, the heat retention/recovery degree were further observed, and individuals who were sufficiently recovered from anesthesia were returned to a breeding cage. The rats were individually identified by an ear punching method and identified by cage cards. For a control group, a solvent (a physiological saline solution), and for a positive control, sake yeast powder (manufactured by Mitsubishi Gas Chemical Company, Inc.) and *Bifidobacterium longum* ATCC BAA-999 were used.

<Test Method>

Each test sample was administered by a forced oral administration method through a gastric tube by using a disposable syringe. As illustrated in Table 1 below, the liquid dosage of the sample was calculated to be 5 mL/kg or 10 mL/kg on the basis of the body weight on the day before administration. Measurement data of movement amounts and brain waves were recorded for 7 hours from 30 min before light was turned off on the day before administration of the test sample and on the day of the administration. On the day of the administration, the sample was orally administered before measurement start, and then, the measurement was started. On the first day (the previous day), for a control, only a solvent was administered, and measurement was performed, and on the next day, the test sample dissolved in a physiological saline solution was administered, and measurement was performed. On the basis of measurement results of the movement amount, it was confirmed that the samples exhibited sedative effects, respectively at different time points. Next, the presence/absence of the sleep promoting effect was examined by combining the measurement result of the movement amount and the measurement result of the electroencephalogram, the electromyogram, and the electrocardiogram. States of being awake, non-REM sleep, and REM sleep were determined in accordance using a standard method (Kohtoh et al., Sleep Biol Rhythms. 2008; 6:163-171) by using sleep analysis software "SleepSign" manufactured by KISSEI COMTEC Co., Ltd. The electroencephalogram data was analyzed up to 6 hours after administration, and the time of being awake, non-REM sleep, and REM sleep was calculated every hour.

TABLE 1

| Group | Test Sample | Dosage | Liquid Dosage | Number of Animals |
|---|---|---|---|---|
| Negative control group | Solvent (Physiological Saline Solution) | 0 mg/kg | 5 mL/kg | 6 |
| Positive Control 1 | Sake Yeast | 200 mg/kg | 10 mL/kg | 6 |
| Positive Control 2 | ATCC BAA-999 | $10^9$ cfu/rat | 5 mL/kg | 6 |
| Test Group | MCC1274 | $10^9$ cfu/rat | 5 mL/kg | 6 |

<Statistical Analysis>

In the obtained numerical values of the movement amounts, and brain waves, the average value of each group was calculated. The awake time, the REM sleep time, the non-REM sleep time, and the movement amount for each hour were tested by Student's t-test with respect to the value on the previous day (not administered). The significant difference between groups was tested by Student's t-test with respect to the control group. The significance level was set as a risk rate of 5%.

<Results>

(1) Negative Control Group

Sleep measurement results of the negative control group are noted in Table 2 (*, $p<0.05$).

TABLE 2

Measurement Result of Negative Control Group

| | Awake (min/h) | | REM sleep (min/h) | | Non-REM sleep (min/h) | | movement amount (counts/h) | |
|---|---|---|---|---|---|---|---|---|
| | Previous day | The day | Previous day | The day | Previous day | The day | Previous day | The day |
| 1 h after administration | 46.7 | 52.2 | 3.2 | 0.9 | 10.2 | 6.9 | 4018 | 4128 |
| 2 h after administration | 50.7 | 47.8 | 1.5 | 2.4 | 7.8 | 9.8 | 5231 | 5807 |
| 3 h after administration | 50.0 | 48.2 | 1.7 | 3.0 | 8.3 | 8.8 | 4382 | 4144 |
| 4 h after administration | 48.4 | 43.4 | 2.0 | 3.4 | 9.6 | 13.2 | 4221 | 3827 |
| 5 h after administration | 42.6 | 47.2 | 4.0 | 2.2 | 13.4 | 10.6 | 3616 | 3928 |
| 6 h after administration | 51.7 | 42.5 | 1.1 | 3.6 | 7.2 | 15.9 | 5352 | 3512 |
| 7 h after administration | 42.8 | 41.9 | 2.2 | 4.8 | 15.0 | 14.9 | 3168 | 4087 |

*, $p < 0.05$

There was no statistically significant change in the negative control group.

(2) Positive Control Group 1 (Sake Yeast)

Sleep measurement results of the positive control group (sake yeast) are noted in Table 3.

TABLE 3

Measurement Result of Positive Control Group 1 (Sake Yeast)

| | Awake (min/h) | | REM sleep (min/h) | | Non-REM sleep (min/h) | | movement amount (counts/h) | |
|---|---|---|---|---|---|---|---|---|
| | Previous day | The day | Previous day | The day | Previous day | The day | Previous day | The day |
| 1 h after administration | 44.9 | 53.3 | 3.1 | 1.4 | 12.0 | 5.3 | 4612 | 4085 |
| 2 h after administration | 50.2 | 48.5 | 1.5 | 2.3 | 8.3 | 9.2 | 4635 | 4739 |
| 3 h after administration | 46.8 | 42.5 | 2.3 | 3.7 | 11.0 | 13.8 | 3588 | 3677 |
| 4 h after administration | 50.2 | 43.0 | 1.1 | 3.9 | 8.6 | 13.0 | 3487 | 3932 |
| 5 h after administration | 49.9 | 45.3 | 1.6 | 3.2 | 8.4 | 11.5 | 3636 | 3243* |
| 6 h after administration | 47.4 | 39.4 | 2.1 | 6.2 | 10.5 | 14.4 | 4541 | 3137* |
| 7 h after administration | 41.5 | 40.4 | 3.5 | 4.8 | 15.0 | 14.8 | 2966 | 2797 |

*$p < 0.05$

In the positive control group 1 (sake yeast), REM sleep and non-REM sleep were slightly increased at the 3-6 hr time points after administration, but a statistically significant difference was not found. The movement amount was reduced in the 5-6 hr points after administration.

(3) Positive Control Group 2 (ATCC BAA-999)

Sleep measurement results of the positive control group 2 (ATCC BAA-999) are noted in Table 4.

TABLE 4

Measurement Result of Positive Control Group 2 (ATCC BAA-999)

| | Awake (min/h) | | REM sleep (min/h) | | Non-REM sleep (min/h) | | movement amount (counts/h) | |
|---|---|---|---|---|---|---|---|---|
| | Previous day | The day | Previous day | The day | Previous day | The day | Previous day | The day |
| 1 h after administration | 50.5 | 52.3 | 2.1 | 1.7 | 7.3 | 6.1 | 4396 | 4985 |
| 2 h after administration | 50.9 | 47.4 | 2.6 | 3.6* | 6.5 | 9.1 | 4900 | 4223 |
| 3 h after administration | 47.1 | 51.2 | 3.8 | 2.0 | 9.1 | 6.8 | 4079 | 4596 |
| 4 h after administration | 45.9 | 45.1 | 3.6 | 4.2 | 10.6 | 10.7 | 3707 | 3434 |
| 5 h after administration | 40.5 | 45.6 | 5.8 | 5.0 | 13.8 | 9.5 | 3257 | 4280 |
| 6 h after administration | 47.6 | 44.5 | 3.5 | 6.0 | 8.9 | 9.5 | 4302 | 3580 |
| 7 h after administration | 42.6 | 46.0 | 5.0 | 4.5 | 13.0 | 9.5 | 3333 | 4061 |

*p < 0.05

In the positive control group 2 (ATCC BAA-999), a statistically significant difference (p<0.05) was found in the increase of REM sleep at a point in time of 2 hours after administration. Meanwhile, 5 h, and 7 h after administration, non-REM sleep was reduced, and a tendency for being awake was found.

(4) Test Group (MCC1274)

Sleep measurement results of the test group (MCC1274) are noted in Table 5.

TABLE 5

Sleep Measurement Result of Test Group 2 (MCC1274)

| | Awake (min/h) | | REM sleep (min/h) | | Non-REM sleep (min/h) | | movement amount (counts/h) | |
|---|---|---|---|---|---|---|---|---|
| | Previous day | The day | Previous day | The day | Previous day | The day | Previous day | The day |
| 1 h after administration | 49.6 | 52.0 | 3.0 | 0.7 | 7.4 | 5.4 | 4464 | 4633 |
| 2 h after administration | 50.1 | 49.4 | 1.4 | 2.8 | 8.5 | 9.3 | 4320 | 4331 |
| 3 h after administration | 44.7 | 47.4 | 4.0 | 2.4 | 11.3 | 9.1 | 3583 | 4184 |
| 4 h after administration | 46.6 | 40.4 | 2.8 | 5.1 | 10.6 | 13.2 | 3607 | 3350* |
| 5 h after administration | 43.1 | 43.4 | 3.9 | 4.5 | 13.0 | 12.9 | 3165 | 3007* |
| 6 h after administration | 53.4 | 45.4* | 1.2 | 5.0* | 5.4 | 13.8* | 4150 | 4137 |
| 7 h after administration | 40.3 | 46.8 | 4.3 | 2.4 | 15.3 | 8.3 | 2488 | 2794 |

*p < 0.05

In the test group (MCC1274), the awake time was reduced at 4 hr and 6 hr time points after administration, and the movement amount was reduced at 4-6 hr after administration, thereby exhibiting the sleep increasing effect. At a point in time of 6 h after administration, a statistically significant difference was found in each of reduction of awake time, REM sleep increase, and non-REM sleep increase (p<0.05).

From the above results, it was found that administration of bacteria belonging to *Bifidobacterium breve* reduced the movement amount during sleep, shortened the awake time during sleep, induced REM sleep, and induced non-REM sleep. In sake yeast or *Bifidobacterium longum* ATCC BAA-999, which was used for the positive control, no significant difference was found in the awake time and the non-REM sleep, and thus, a high sleep promoting effect was recognized even compared to these.

Experimental Example 2

In Experimental Example 2, for humans as targets, the sleep promoting effect of bacteria belonging to *Bifidobacterium breve* was verified.

<Production of Test Sample>

A dried product of live bacteria produced by the same method as in the above Experimental Example 1 was mixed with starch, and 345 mg was filled into one capsule to obtain a test sample.

Meanwhile, a placebo capsule in which 345 mg of only starch was filled into the capsule was produced, and this was set as a control sample.

It was confirmed that the test sample and the control sample were indistinguishable in appearance, color, and taste.

<Subject>

Healthy people aged 20 or older (BMI: 25 or more and less than 30) were registered as subjects in a clinical trial. Further, people who did not violate the following exclusion criteria (1) to (7) through body composition measurement, blood tests, and medical examination by interview by intention were set as analysis targets.

(1) A person who is being treated for a serious disease, etc. or a person having such a serious past medical history (2) A person who is suffering from a gastrointestinal disease, and is taking medication (3) A person who is receiving drug treatment for a lifestyle disease (diabetes, hypertension, or dyslipidemia)

(4) A person having a past medical history of drug allergy or serious food allergy (5) A pregnant person, a person who is willing to be pregnant during a test period, or a breast-feeding person (6) A heavy smoker, a heavy drinker, or a person with irregular lifestyles (7) A person who is judged to be unsuitable as a subject by a doctor responsible for the test or a doctor in charge of the test, on the basis of the subject background, physical findings, or results of medical examination by interview, etc.

Table 6 below illustrates specific background factors of subjects. No significant difference was recognized in ages between the target group and the test group.

TABLE 6

| | Control group | Test group | Inter-group difference |
|---|---|---|---|
| Number of subjects | 40 | 40 | N.S. |
| Age | 45.6 ± 8.5 | 45.4 ± 9.8 | N.S. |

<Test Method>

*Bifidobacterium breve* MCC1274 was administered to healthy adult men and women as targets, and the effect on sleep before and after ingestion was examined. The subject ingested the test sample or the control sample together with water, etc. once a day for 12 weeks, within 30 min after a meal. That is, the intake per day in the test group was set as 20 billion live bacteria of *Bifidobacterium breve* MCC1274 (FERN BP-11175).

Before ingestion, and on the 12th week after ingestion, Pittsburgh Sleep Quality Index (PSQI) was used to calculate a total score of seven factors of sleep quality, sleep onset time, sleep time, sleep efficiency, sleep difficulty, use of sleeping pills, and difficulty in daytime awakening.

<Results>

Table 7 illustrates average values of the total scores of Pittsburgh Sleep Quality Index (PSQI) before and after ingestion of *Bifidobacterium breve*, and a change amount.

TABLE 7

| Before Ingestion | After Ingestion | Change Amount |
| --- | --- | --- |
| 3.1 | 2.9 | −0.2 |

As illustrated in Table 7, the total score of PSQI was reduced by −0.20 after ingestion for 12 weeks as compared to before ingestion of the test substance, and thus sleep quality, sleep onset time, sleep time, sleep efficiency, use of sleeping pills, and difficulty in daytime awakening were improved on the whole.

Furthermore, Table 8 below illustrates the average value of scores for each item in PSQI.

TABLE 8

Average Value of Scores for Each PSQI Item

| | Sleep quality (C1) | Sleep onset time (C2) | Sleep time (C3) | Sleep efficiency (C4) | Use of sleeping pills (C6) | Difficulty in day time awakening (C7) |
| --- | --- | --- | --- | --- | --- | --- |
| Before Ingestion | 0.88 | 0.40 | 0.88 | 0.13 | 0 | 0.83 |
| After Ingestion | 0.88 | 0.43 | 0.78 | 0.10 | 0 | 0.73* |

*p < 0.05, Wilcoxon's signed-ranks test

As illustrated in Table 8, sleep time (C3), and sleep efficiency (C4) were improved as compared to before ingestion, and in particular, for difficulty in daytime awakening (C7), significant improvement was observed as compared to before ingestion.

From the above results, it was found that ingestion of bacteria belonging to *Bifidobacterium breve* improved the sleep quality and the sleep status on the whole. In particular, the results of sleep time (C3) and sleep efficiency (C4) (calculated from a difference between wake-up time and bedtime) in scores for each item suggest that the sleep time was prolonged, and as a result, it is found that the symptom of difficulty in daytime awakening (C7), such as becoming unable to wake up when sleeping is prohibited (during car driving, eating, social activities, etc.) or not sustaining the motivation required to complete things was improved.

Production Example

Hereinafter, production examples of a sleep-promoting composition, a medical composition, and a food composition will be described.

Production Example 1

*Bifidobacterium breve* MCC1274 (FERM BP-11175) is added to 3 mL of MRS liquid medium, and is anaerobically cultured at 37° C. for 16 h. Then, the culture solution is concentrated, and freeze-dried to obtain freeze-dried powder of bacteria (bacterial powder). The bacterial powder is uniformly mixed with a whey protein concentrate (WPC) and prebiotics (lactulose, raffinose and galactooligosaccharides) to obtain a composition. 20 g of the corresponding composition is dissolved in 200 g of water so as to obtain a sleep-promoting composition. By administration of the corresponding composition, sleep may be promoted.

Production Example 2

*Bifidobacterium breve* MCC1274 (FERM BP-11175) is added to 3 mL of MRS liquid medium, and is anaerobically cultured at 37° C. for 16 h. Then, the culture solution is concentrated, and freeze-dried to obtain freeze-dried powder of bacteria (bacterial powder). The bacterial powder is uniformly mixed with dry powder of a milk protein concentrate (MPC480, manufactured by Fonterra, protein content 80% by mass, casein protein:whey protein=about 8:2), and prebiotics (lactulose, raffinose and galactooligosaccharides) to obtain a composition. 20 g of the corresponding composition is dissolved in 200 g of water to obtain a sleep-promoting composition.

Production Example 3

*Bifidobacterium breve* MCC1274 (FERM BP-11175) is added to 3 mL of MRS liquid medium, and is anaerobically cultured at 37° C. for 16 h. Then, the culture solution is concentrated, and freeze-dried to obtain freeze-dried powder of bacteria (bacterial powder). Then, prebiotics (lactulose, raffinose and galactooligosaccharides), and crystalline cellulose are put into a stirring granulator and mixed. Then, granulation is performed with addition of purified water, and the granulated product is dried. Then, the granulated product (a medical composition) that contains an extract component of bacteria and prebiotics, and contains an excipient is obtained. By administration of the corresponding granulated product, sleep may be promoted.

Production Example 4

A method of producing fermented milk to which *Bifidobacterium breve* MCC1274 (FERM BP-11175) is added will be described below.

First, a milk raw material is mixed with water, other components, or the like as necessary, and is preferably subjected to a homogenization treatment and a heat-sterilization treatment. The homogenization treatment and the heat-sterilization treatment may be performed by conventional methods. A *lactobacilli* starter is added (inoculated) to the sterilized milk preparation obtained through heat-sterilization, and fermentation is performed while a predetermined fermentation temperature is maintained, so that a fermented product is obtained. By the fermentation, curds are formed.

As for the *lactobacilli* starter, for example, *lactobacilli* generally used for yogurt production, such as *Lactobacillus bulgaricus, Lactococcus lactis*, and *Streptococcus thermophilus* may be used. When pH reaches a target value, the formed curds are crushed by stirring, and cooled to 10° C. or less to obtain a fermented product. By cooling to 10° C. or less, the activation of *lactobacilli* may be reduced, and the production of acid may be suppressed.

Then, the fermented product obtained through the fermentation process is subjected to heat treatment to obtain a heated fermented product (a heat-treated fermented product). By properly heating the fermented product, it is possible to suppress acid from being produced by *lactobacilli* in the heated fermented product. Accordingly, during the subsequent production process and/or during storage of concentrated fermented milk including bifidobacteria, reduction of pH may be suppressed, and as a result, the viability of bifidobacteria may be improved.

Next, *Bifidobacterium breve* MCC1274 (FERM BP-11175) and prebiotics (lactulose, raffinose and galactooligosaccharides) are added to the heated fermented product obtained through the heat treatment process. The addition amount of *Bifidobacterium breve* MCC1274 (FERM BP-11175) is preferably $1 \times 10^7$ to $1 \times 10^{11}$ CFU/mL, more preferably $1 \times 10^8$ to $1 \times 10^{10}$ CFU/mL with respect to the heated fermented product. When the *Bifidobacterium breve* (NITE BP-02622, NITE BP-11175) are dead bacteria, CFU/mL may be replaced with individual cells/mL.

After *Bifidobacterium breve* MCC1274 (FERM BP-11175) and prebiotics are added to the heated fermented product, concentration is performed. The concentration process may be performed by properly using a conventionally known concentration method. In the centrifugal separation method, whey in the concentration target (the heated fermented product to which bifidobacteria and prebiotics are added) is removed to obtain concentrated fermented milk comprising bifidobacteria and prebiotics in which the solid content concentration is increased. By ingestion of the obtained fermented milk, sleep may be promoted.

Production Example 5

A method of producing modified milk powder to which *Bifidobacterium breve* MCC1274 (FERM BP-11175) is added will be described below.

10 kg of desalted milk whey protein powder (manufactured by Mirai), 6 kg of milk casein powder (manufactured by Fonterra), 48 kg of lactose (manufactured by Mirai), 920 g of a mineral mixture (manufactured by Tomita Pharmaceutical Co., Ltd.), 32 g of a vitamin mixture (manufactured by Tanabe Seiyaku Co., Ltd.), 500 g of lactulose (manufactured by Morinaga Milk Industry Co., Ltd.) 500 g of raffinose (manufactured by Nippon Beet Sugar Manufacturing Co., Ltd.), and 900 g of galactooligosaccharide liquid sugar (manufactured by Yakult Pharmaceutical Industry Co., Ltd.) are dissolved in 300 kg of warm water, and then dissolved at 90° C. for 10 min through heating, and homogenized with addition of 28 kg of prepared fat (manufactured by Taiyo Yushi Corp.). Then, sterilization, and concentration steps are performed, and about 95 kg of modified milk powder is prepared through spray-drying. To this, 100 g of microbial cell powder of *Bifidobacterium breve* MCC1274 (FERM BP-11175) ($1.8 \times 10^{11}$ cfu/g, manufactured by Morinaga Milk Industry Co., Ltd.), which is triturated with starch, is added to prepare about 95 kg of modified milk powder blended with bifidobacteria and oligosaccharides. When the obtained modified milk powder is dissolved in water, and becomes a milk preparation at a total solid content concentration of 14% (w/V) (as a standard milk preparation concentration), the number of bifidobacteria in the milk preparation may become $2.7 \times 10^9$ cfu/100 ml. When the modified milk powder obtained as described above is administered, sleep may be promoted.

The invention claimed is:

1. A method of promoting sleep in a subject comprising administering a composition comprising bacteria belonging to *Bifidobacterium breve* as an active ingredient to the subject, wherein the subject has a condition that results from poor sleep,
    wherein the bacteria are *Bifidobacterium breve* MCC1274 (FERM BP-11175).
2. The method of claim 1, wherein said composition is formulated as a medicine.
3. The method of claim 1, wherein said composition is a food or drink.
4. The method of claim 1, wherein the subject is a person over 35 years old.
5. The method of claim 1, wherein said condition that results from poor sleep is selected from the group consisting of insomnia, hypersomnia, a circadian rhythm sleep disorder, a restless legs syndrome (*anxietas tibiarum*), snoring, a sleep apnea syndrome, parasomnia, narcolepsy, sleepwalking (somnambulism), confusion arousal, a sleep terror disorder (night terror), a rhythmic movement disorder, cramps during sleep, sleep talking, night crying, infant colic (colic), nocturnal leg cramps, nightmare, sleep paralysis, sleep-related penile erectile dysfunction, an REM sleep behavior disorder, bruxism, nocturnal enuresis, paroxysmal dystonia, a periodic limb movement disorder, a sudden infant death syndrome (SIDS), and combinations thereof.

* * * * *